United States Patent
Harth et al.

(10) Patent No.: US 7,198,634 B2
(45) Date of Patent: Apr. 3, 2007

(54) PHOTOTHERAPEUTIC TREATMENT OF SKIN CONDITIONS

(75) Inventors: Yoram Harth, Haifa (IL); Avner Korman, Herzlia (IL)

(73) Assignee: Curelight Ltd., Or-Akiva (IL)

( * ) Notice: Subject to any disclaimer, the term of this patent is extended or adjusted under 35 U.S.C. 154(b) by 62 days.

(21) Appl. No.: 10/951,358

(22) Filed: Sep. 28, 2004

(65) Prior Publication Data

US 2005/0090877 A1    Apr. 28, 2005

Related U.S. Application Data

(63) Continuation-in-part of application No. 10/674,313, filed on Sep. 30, 2003, now abandoned, which is a continuation-in-part of application No. 10/366,452, filed on Feb. 13, 2003, now abandoned, and a continuation-in-part of application No. 10/098,592, filed on Mar. 18, 2002, now abandoned, application No. 10/951,358, and a continuation-in-part of application No. 10/007,702, filed on Dec. 10, 2001, now abandoned, which is a continuation-in-part of application No. 09/756,130, filed on Jan. 9, 2001, now Pat. No. 6,835,202, which is a continuation-in-part of application No. PCT/IL99/00374, filed on Jul. 7, 1999, now abandoned.

(51) Int. Cl.
   *A61N 5/01* (2006.01)
(52) U.S. Cl. ............................ 607/90; 128/898; 607/88
(58) Field of Classification Search ................ 128/898; 606/9; 607/88–94
   See application file for complete search history.

(56) References Cited

U.S. PATENT DOCUMENTS

| | | | |
|---|---|---|---|
| 2,183,726 A | | 2/1939 | Sommer et al. |
| 3,867,948 A | * | 2/1975 | Kallenborn ................ 607/88 |
| 4,229,658 A | | 10/1980 | Gonser |
| 4,407,282 A | | 10/1983 | Swartz |
| 4,930,504 A | | 6/1990 | Diamantopoulos et al. |
| 5,247,533 A | * | 9/1993 | Okazaki et al. .......... 372/45.01 |
| 5,576,013 A | | 11/1996 | Williams et al. |
| 5,591,219 A | | 1/1997 | Dungan |
| 5,620,478 A | | 4/1997 | Eckhouse |
| 5,707,401 A | | 1/1998 | Talmore |
| 5,736,582 A | | 4/1998 | Devillez |
| 5,800,479 A | | 9/1998 | Thiberg |

(Continued)

FOREIGN PATENT DOCUMENTS

EP    0 105 584 A1    4/1984

(Continued)

OTHER PUBLICATIONS

V. Sigurdsson et al., "Phototherapy of Acne Vulgaris with Visible Light", Dermatology 1997; 194:256-260, Pharmacology and Treatment.

(Continued)

*Primary Examiner*—Henry M Johnson, III
(74) *Attorney, Agent, or Firm*—Watov & Kipnes, P.C.

(57) ABSTRACT

A method for treating an inflammation in skin of a patient includes irradiating the skin with infrared (IR) radiation in a first wavelength band and with violet/blue light in a second wavelength band.

36 Claims, 7 Drawing Sheets

U.S. PATENT DOCUMENTS

| | | | |
|---|---|---|---|
| 5,843,143 A | 12/1998 | Whitehurst | |
| 5,896,457 A | 4/1999 | Tyrrel | |
| 6,063,108 A | 5/2000 | Salansky et al. | |
| 6,183,500 B1 | 2/2001 | Kohler | |
| 6,223,071 B1 | 4/2001 | Lundahl et al. | |
| 6,235,016 B1 | 5/2001 | Stewart | |
| 6,248,733 B1 | 6/2001 | Landgrebe et al. | |
| 6,269,818 B1 | 8/2001 | Lui et al. | |
| 6,324,418 B1 | 11/2001 | Crowley et al. | |
| 6,443,978 B1 | 9/2002 | Zharov | |
| 6,602,275 B1 | 8/2003 | Sullivan | |
| 6,663,659 B2 * | 12/2003 | McDaniel | 607/88 |
| 6,676,655 B2 * | 1/2004 | McDaniel | 606/9 |
| 6,866,678 B2 * | 3/2005 | Shenderova et al. | 607/88 |
| 6,872,221 B2 * | 3/2005 | Lytle | 607/89 |
| 6,887,260 B1 * | 5/2005 | McDaniel | 607/88 |
| 6,896,693 B2 * | 5/2005 | Sullivan | 607/91 |
| 2002/0002391 A1 * | 1/2002 | Gerdes | 607/89 |
| 2003/0004499 A1 * | 1/2003 | McDaniel | 606/3 |
| 2003/0004556 A1 * | 1/2003 | McDaniel | 607/88 |
| 2004/0034397 A1 * | 2/2004 | Lin | 607/94 |
| 2004/0068305 A1 * | 4/2004 | Bansal et al. | 607/89 |

FOREIGN PATENT DOCUMENTS

| | | |
|---|---|---|
| GB | 2 272 278 A | 5/1994 |
| WO | WO 95/16454 | 6/1995 |
| WO | WO 96/14899 | 5/1996 |

OTHER PUBLICATIONS

Monica Elman, Michael Slatkine and Yoram Harth, "The Effective Treatment of Acne Vulgaris by a High-Intensity, Narrow Band 405-420 nm Light Source", Nov. 27, 2002, pp. 111-116.

Lon R. Horwitz, DPM, CWS; Thomas J. Burke, PhD; and Dale Carnegie, DPM, "Augmentation of Wound Healing Using Monochromatic Infrared Energy", Jan./Feb. 1999, pp. 35-40.

* cited by examiner

PHOTOTHERAPEUTIC TREATMENT OF SKIN CONDITIONS

CROSS-REFERENCE TO RELATED APPLICATIONS

This application is a continuation-in-part application of U.S. patent application Ser. No. 10/674,313 filed Sep. 30, 2003 now abandoned, which is a continuation-in-part application of U.S. patent application No. 10/366,452 filed Feb. 13, 2003 now abandoned, and of U.S. patent application Ser. No. 10/098,592 filed Mar. 18, 2002 now abandoned. These applications are continuations-in-part of U.S. patent application Ser. No. 10/007,702 filed Dec. 10, 2001, which is a continuation-in-part of U.S. patent application Ser. No. 09/756,130 filed Jan. 9, 2001 now U.S. Pat. No. 6,835,202, which is a continuation-in-part of PCT Patent Application No. PCT/IL99/00374 filed Jul. 7, 1999 now abandoned. The disclosures of all these related applications are incorporated herein by reference.

FIELD OF THE INVENTION

The present invention relates generally to skin phototherapy, and specifically to treatment of skin inflammations.

BACKGROUND OF THE INVENTION

It is known in the art to use violet/blue light, in the spectral range between 405 and 450 nm, for treatment of skin conditions, such as acne vulgaris. The *P. Acnes* bacteria, which are the cause of acne skin lesions, produce porphyrins, which become toxic in the presence of light in this range. This method of treating acne is described in the above-referenced related applications, as well as in an article by Elman et al., entitled "The Effective Treatment of Acne Vulgaris by a High-intensity, Narrow Band 405–420 nm Light Source," *Journal of Cosmetic and Laser Therapy* 5 (2003), pages 111–116.

U.S. Pat. No. 6,183,500, to Kohler, whose disclosure is incorporated herein by reference, describes a process and apparatus for the cosmetic treatment of acne vulgaris by irradiating the affected skin areas with light characterized by a combination of two emission spectra, one in a blue region and the other in a red region. The light is generated by low-pressure mercury discharge having two different spectra, one in the blue range from 400 to 450 nm, and the other in the red range from 580 to 659 nm.

The above-mentioned U.S. patent application Ser. No. 10/098,592 (published as US 2002/0173833) describes the use of violet/blue radiation in the range of 400–450 nm to reduce the level of extra-cellular pro-inflammatory cytokines. The inventors indicate that this cytokine-reducing effect may be useful not only in anti-inflammatory treatment of acne sites, but also in treating other inflammatory skin conditions, such as skin ulcers and cutaneous autoimmune diseases.

Shnitkind et al. describe a study into the therapeutic effect of blue light in a poster paper entitled, "Anti-Inflammatory Properties of Narrow Band Blue Light," presented at the Annual Meeting of the US Society of Investigative Dermatology (May, 2002), which is incorporated herein by reference. This study was conducted to investigate the effect of narrow band blue light on the inflammatory process in the presence and absence of cytokines and UVB radiation. (The release of cytokines from cutaneous cells is known to be important in the initiation and development of many inflammatory skin disorders.) The study showed that high-intensity, narrow band blue light has anti-inflammatory effect on keratinocytes by suppressing the cytokine-induced upregulation of IL-1alpha.

Infrared (IR) radiation sources, operating at around 890 nm, have been used to promote healing of different types of skin wounds. This use of IR radiation is described, for example, by Horwitz et al., in "Augmentation of Wound Healing Using Monochromatic Infrared Energy," *Advances in Wound Care* (January/February 1999), pages 35–40, which is incorporated herein by reference. The authors applied monochromatic IR radiation at 890 nm to recalcitrant dermal lesions, including venous ulcers, diabetic ulcers and a wound related to scleroderma. They note that the rate and quality of healing following IR irradiation may be related to local increases in nitric oxide (NO) concentration, which have been demonstrated to correlate with vasodilatory and anabolic responses.

SUMMARY OF THE INVENTION

Embodiments of the present invention provide improved methods and apparatus for treatment of inflammatory skin conditions, by combined irradiation with violet/blue and infrared (IR) radiation. The present invention stems from the realization that swelling due to skin inflammations, such as ulcers, post-resurfacing and post-operative conditions, aging and other lesions, tends to reduce blood and/or lymphatic circulation in the vicinity of the inflammation. The impaired circulation, in turn, exacerbates the inflammatory condition and retards healing. The effectiveness of violet/blue light by itself in reducing levels of pro-inflammatory agents may thus be limited by inadequate circulation in the inflamed area. The addition of IR irradiation, as taught by the present invention, overcomes this limitation by enhancing circulation during the anti-inflammatory violet/blue light treatment.

There is therefore provided, in accordance with an embodiment of the present invention, a method for treating an inflammation in skin of a patient, including irradiating the skin with infrared (IR) radiation in a first wavelength band and with violet/blue light in a second wavelength band.

Typically, the first wavelength band is selected to cause dilation of blood vessels in a vicinity of the inflammation, and irradiating the skin with the violet/blue light includes applying the violet/blue light to the inflammation while the blood vessels are dilated. Irradiating the skin may include irradiating the skin with the IR radiation and the violet/blue light simultaneously or sequentially.

In disclosed embodiments, the first wavelength band is in the range 800–980 nm, and the second wavelength band is in the range 405–450 nm. Typically, the first wavelength band is in the range 850–900 nm. In some embodiments, irradiating the skin includes irradiating the skin with at least 4 mW/cm$^2$ of the violet/blue light and at least 1 mW/cm$^2$ of the IR radiation, and typically with at least 20 mW/cm$^2$ of the violet/blue light and at least 8 mW/cm$^2$ of the IR radiation.

Typically, irradiating the skin includes irradiating the skin continuously for at least one minute. Alternatively, irradiating the skin includes irradiating the skin with pulsed radiation.

In a disclosed embodiment, irradiating the skin includes irradiating the skin using a single radiation source, which emits both the violet/blue light and the IR radiation, wherein the single radiation source includes a discharge lamp containing metal halide materials selected to radiate in the first and second wavelength bands. In another embodiment, irradiating the skin includes irradiating the skin using an array of solid-state radiation sources.

Typically, irradiating the skin includes treating a condition selected from a group of conditions consisting of skin aging, ulcers, edema, rosacea, chronic cutaneous inflammatory conditions and acne. A medicated cream may be applied to the skin in conjunction with irradiating the skin.

In one embodiment, irradiating the skin includes irradiating the skin using a radiation source that is in contact with the skin.

There is also provided, in accordance with an embodiment of the present invention, apparatus for treating an inflammation in skin of a patient, including at least one radiation source, which is adapted to irradiate the skin with infrared (IR) radiation in a first wavelength band and with violet/blue light in a second wavelength band.

In a disclosed embodiment, the at least one radiation source includes a single radiation source, which emits both the violet/blue light and the IR radiation. Typically, the single radiation source includes a discharge lamp containing metal halide materials selected to radiate in the first and second wavelength bands, wherein the metal halide materials may include gallium and cesium halides.

In another embodiment, the at least one radiation source includes a plurality of radiation sources, and the apparatus includes an adjustable bracket, on which the radiation sources are mounted, so as to allow a relative angular orientation of the radiation sources to be adjusted. Typically, the bracket is adjustable so as to direct at least two of the radiation sources to irradiate a common region of the skin, and so as to direct the at least two of the radiation sources to irradiate different regions of the skin.

Additionally or alternatively, the plurality of radiation sources includes an array of solid-state radiation sources, including first radiation sources, which emit the radiation in the first wavelength band, and second radiation sources, which emit the radiation in the second wavelength band. Typically, the solid-state radiation sources are selected from a group of sources consisting of light-emitting diodes (LEDs) and laser diodes. In a disclosed embodiment, the first radiation sources include at least one of GaAs and GaAlAs diodes, while the second radiation sources includes at least one of GaN, SiN, InSiN, and SiC diodes.

Typically, the at least one radiation source includes a spectral filter, for blocking ultraviolet (UV) radiation generated by the at least one radiation source. Additionally or alternatively, the at least one radiation source includes a forced air cooling device for cooling the skin that is irradiated by the at least one radiation source. Further additionally or alternatively, the at least one radiation source is adapted to be placed in contact with the skin.

There is additionally provided, in accordance with an embodiment of the present invention, a lamp, including:

an envelope, which is at least partly transparent;

an excitation circuit, which is coupled to the lamp so as excite an electrical discharge within the envelope; and a gas and metal mixture, contained within the envelope, which is adapted, upon excitation of the electrical discharge by the excitation circuit, to emit both narrowband infrared (IR) radiation in a first wavelength band and narrowband violet/blue light in a second wavelength band.

Typically, the first wavelength band is in the range 800–980 nm, and the second wavelength band is in the range 405–450 nm. In a disclosed embodiment, the first wavelength band is in the range 850–910 nm.

In some embodiments, the gas mixture includes metal halide materials selected to radiate in the first and second wavelength bands. Typically, the metal halide materials include gallium and cesium halides. Additionally or alternatively, the gas mixture further includes mercury. Further additionally or alternatively the excitation circuit includes electrodes, which are spaced a predetermined distance apart within the envelope.

The present invention will be more fully understood from the following detailed description of the embodiments thereof, taken together with the drawings in which:

DETAILED DESCRIPTION OF EMBODIMENTS

Figure 1:
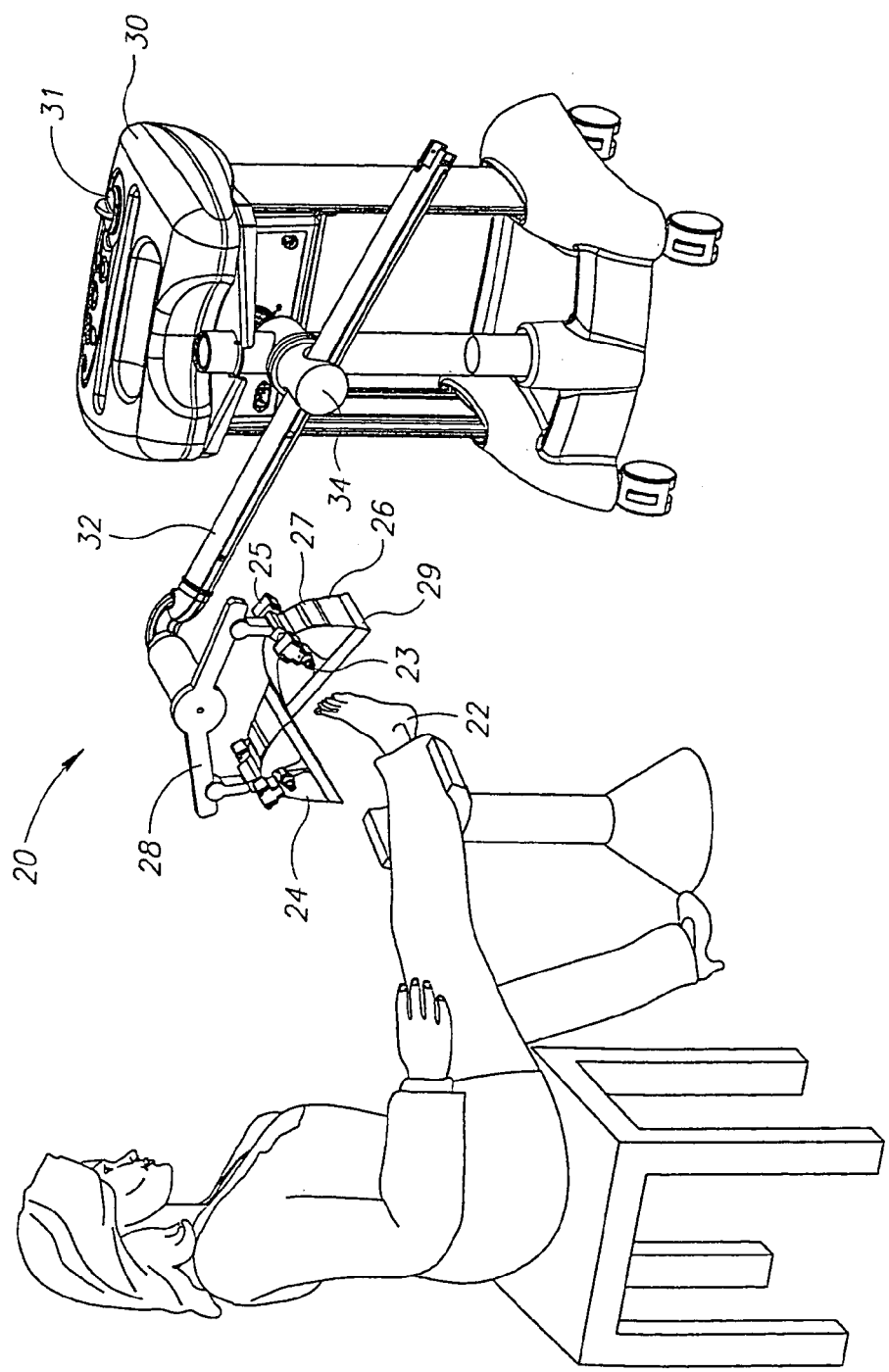
FIG. 1 is a schematic, pictorial illustration of a system for phototherapy, in accordance with an embodiment of the present invention.

FIG. 1 is a schematic, pictorial illustration of a system 20 for phototherapy, in accordance with an embodiment of the present invention. System 20 is used to treat inflammations of the skin, such as an ulcer on a leg 22 of a patient. The system in this embodiment comprises two radiators 24 and 26, each comprising a lamp 23, a lamp holder 25, a reflector 27 and an optical filter 29, which are described in greater detail herein below. Each radiator may be enclosed in a metal or a plastic housing, not shown here. Typically, both of radiators 24 and 26 emit both violet/blue and IR radiation. Alternatively, one of the radiators may emit violet/blue radiation, while the other emits IR radiation. Further alternatively, system 20 may comprise only a single radiator (emitting both violet/blue and IR) or three or more radiators.

Radiators 24 and 26 are mounted on an adjustable bracket 28, which allows the positions and angular orientations of the radiators to be adjusted. Thus, bracket 28 may be set so that both radiators are aimed toward the same region of the patient's skin, as shown in FIG. 1. Alternatively, bracket 28 may be adjusted so that each radiator irradiates a different region, so that a large area of the skin can be treated at one time. Bracket 28 and radiators 24 and 26 are coupled to a control and power supply console unit 30 by an adjustable arm 32 and a joint module 34. The arm and joint module together permit flexible 3D positioning of the radiators, so as to enable treatment of all body parts of both seated and reclining patients. The console 30 comprises a power supply module for operating the radiators and user controls 31 for setting treatment parameters, such as the treatment duration and power level of irradiation.

Typically, radiators 24 and 26 emit violet/blue light in the range of 405–450 nm, for anti-inflammatory effect, and IR radiation in the range of 800–980 nm for vascular dilation. Preferably, radiators 24 and 26 are narrowband sources, meaning that most of the radiation emitted by the radiators falls within bands no more than 100 nm wide in the violet/blue and IR spectral ranges. Most preferably, most of the IR radiation is emitted in a band between 850 and 910 nm. Absorption of radiation in this wavelength range by hemoglobin in the blood is believed to cause the hemoglobin to release NO (nitric oxide), which is then absorbed in the blood vessel walls, causing them to dilate. The lifetime of NO in the blood is approximately 10 sec. Therefore, the effect of the IR irradiation by radiators 24 and 26 is local and temporary. To take advantage of this effect, the radiators may either emit the violet/blue and IR radiation simultaneously, or they may emit the IR and violet/blue radiation in sufficiently rapid succession so that the violet/blue radiation is applied while the blood vessels are dilated.

For effective treatment of skin inflammation, the violet/blue light intensity on the patient's skin should typically be at least 4 mW/cm$^2$, while the IR intensity is at least 1 mW/cm$^2$. For more rapid treatment, the violet/blue light intensity may be 20 mW/cm$^2$ or greater, while the IR intensity is 9 mW/cm$^2$ or greater. Typically, the radiators are set to operate continuously for periods of one minute or more. Alternatively, the radiators may operate in pulsed modes, with accumulated pulse intensities of at least 200 mJ/cm$^2$ in the violet/blue range and 60 mJ/cm$^2$ in the IR. The treatment area is determined by the area of the inflammation, and typically varies between about 5×5 and 30×30 cm. The total radiation dosage depends on the type of condition and its extent. For healing skin ulcers, for example, a regimen of daily treatments of 30 minutes each over a period of two to three weeks, with a dose per treatment of 30 J/cm$^2$, is believed to be effective.

Figure 2:
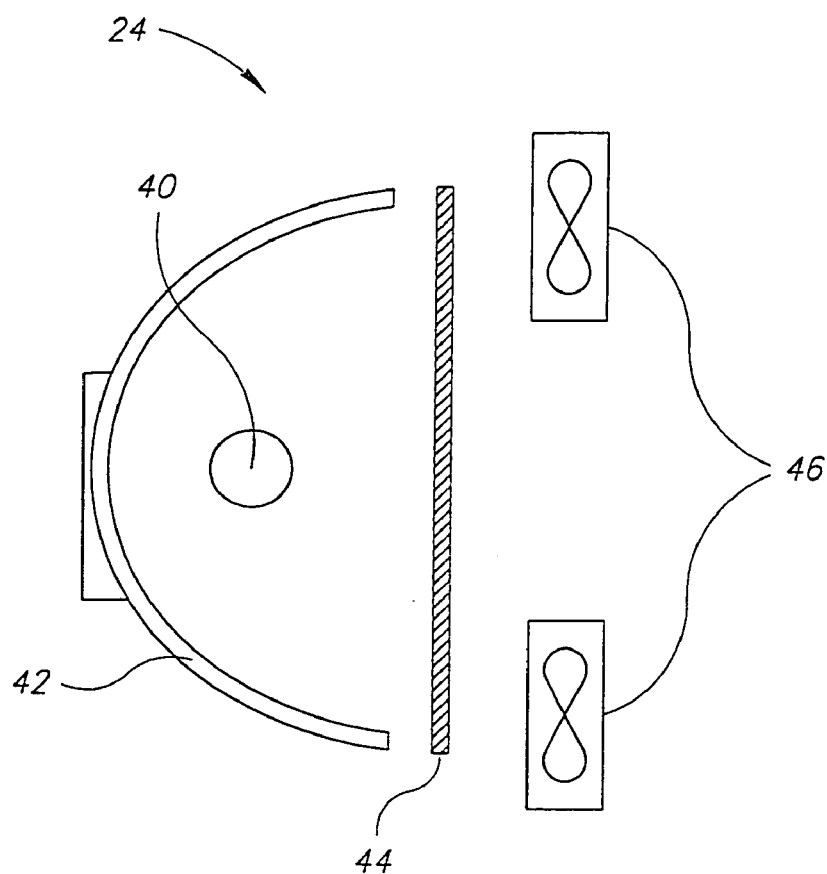
FIG. 2 is a schematic, sectional view of a radiator for use in phototherapy, in accordance with an embodiment of the present invention.

FIG. 2 is a schematic, sectional illustration showing details of radiator 24, in accordance with an embodiment of the present invention. (The same design may be used for radiator 26.) The radiator comprises a lamp 40, typically a gas discharge lamp, which emits both violet/blue and IR radiation, as described further hereinbelow. A reflector 42 collects and reflects the radiated energy from the lamp 40 toward the patient's skin. The reflector may have a parabolic cross-section, for example, or it may be specially designed with multiple curved reflective facets. A filter 44 blocks ultraviolet (UV) radiation output below about 400 nm. Filter 44 may comprise, for example, a GG400 UV-blocking filter, approximately 4 to 6 mm thick, produced by Schott Optics Division (Mainz, Germany). One or more fans 46 or other types of ventilators or blowers may be mounted on radiator 24 in order to cool the treated area of the skin.

Figure 3:
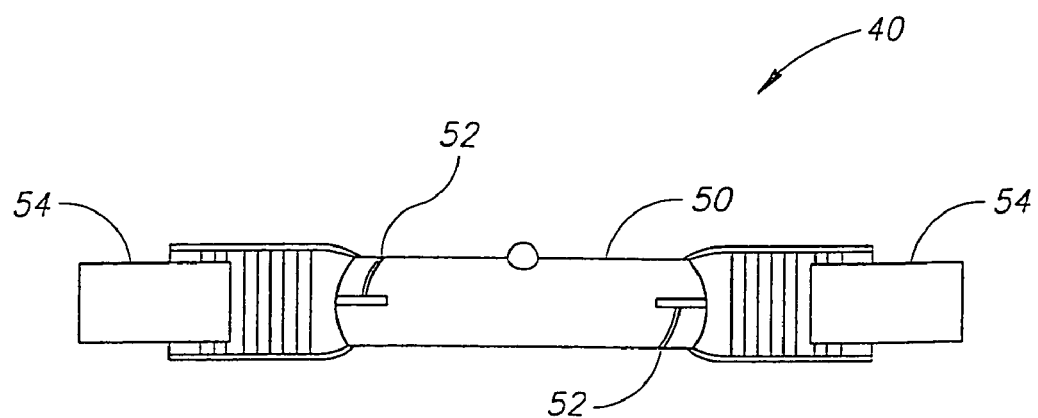
FIG. 3 is a schematic side view of a discharge lamp, in accordance with an embodiment of the present invention.

FIG. 3 is a schematic side view of lamp 40, in accordance with an embodiment of the present invention. The lamp comprises a transparent quartz tube 50, about 8–14 mm in diameter, containing at least two electrodes 52 separated by a gap of about 30 to 40 mm. The electrodes are coupled to terminals 54 so as to define an excitation circuit, which is connected to the power supply that drives the lamp. Typically, the excitation circuit is driven by an electrical current between 3.0 and 3.6 A, at 115 VAC. Alternatively, both higher- and lower-power AC and DC voltage-driven lamps and other types of discharge excitation circuits, as are known in the art, may be used in system 20.

Lamp 40 is filled with a novel combination of gases and metals in order to provide simultaneous violet/blue and IR narrowband emission. Tube 50 is first evacuated to a high vacuum in order to eliminate all atmospheric gases and humidity. The tube is then filled with about 40 mg of pure mercury, about 0.2 mg of a gallium halide, and about 0.1 to 0.5 mg of a cesium halide. The gallium and cesium halides typically comprise bromides or iodides or a combination of the two. The gallium halide causes the lamp to emit strongly on lines in the 405–450 nm range, while the cesium halide causes IR emission on lines in the 850–910 nm range. Depending on the amount of cesium halide in the tube, the IR emission accounts for between 10% and 50% of the total optical power output of the lamp.

Figure 4:
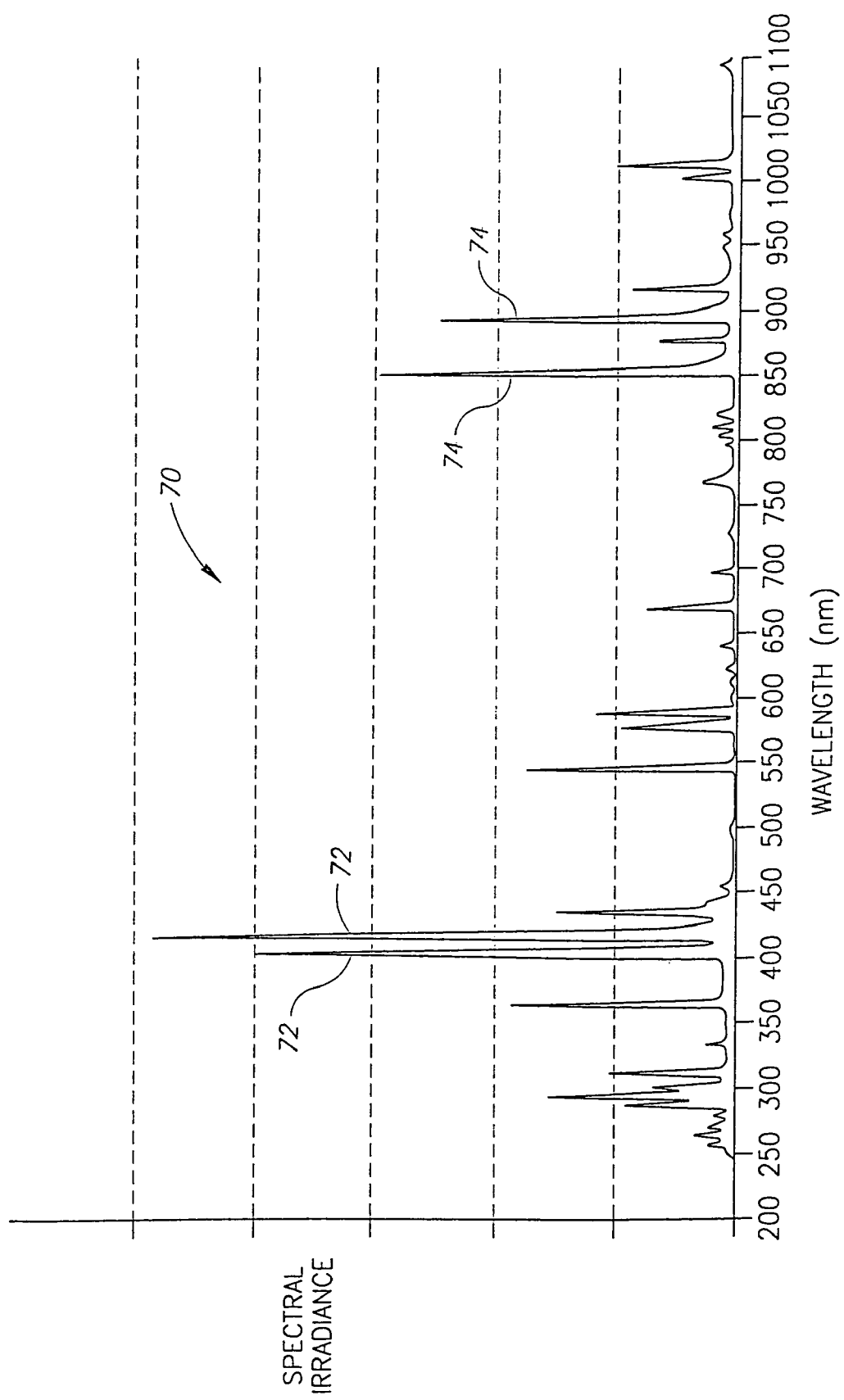
FIG. 4 is a schematic spectral diagram showing an emission spectrum of a discharge lamp, in accordance with an embodiment of the present invention.

FIG. 4 is a schematic typical spectral diagram showing an output spectrum 70 of lamp 40, in accordance with an embodiment of the present invention. Strong violet/blue lines 72 are seen in the 405–450 nm range due to the gallium in the lamp, along with IR lines 74 at 852 nm and 894 nm due to the cesium.

A lamp produced to the above specifications by Lamptech Ltd. (Ashkelon, Israel) gave optical power density on the skin, when installed in system 20, over 30 mW/cm$^2$ in the violet/blue and IR bands together.

Figure 5:
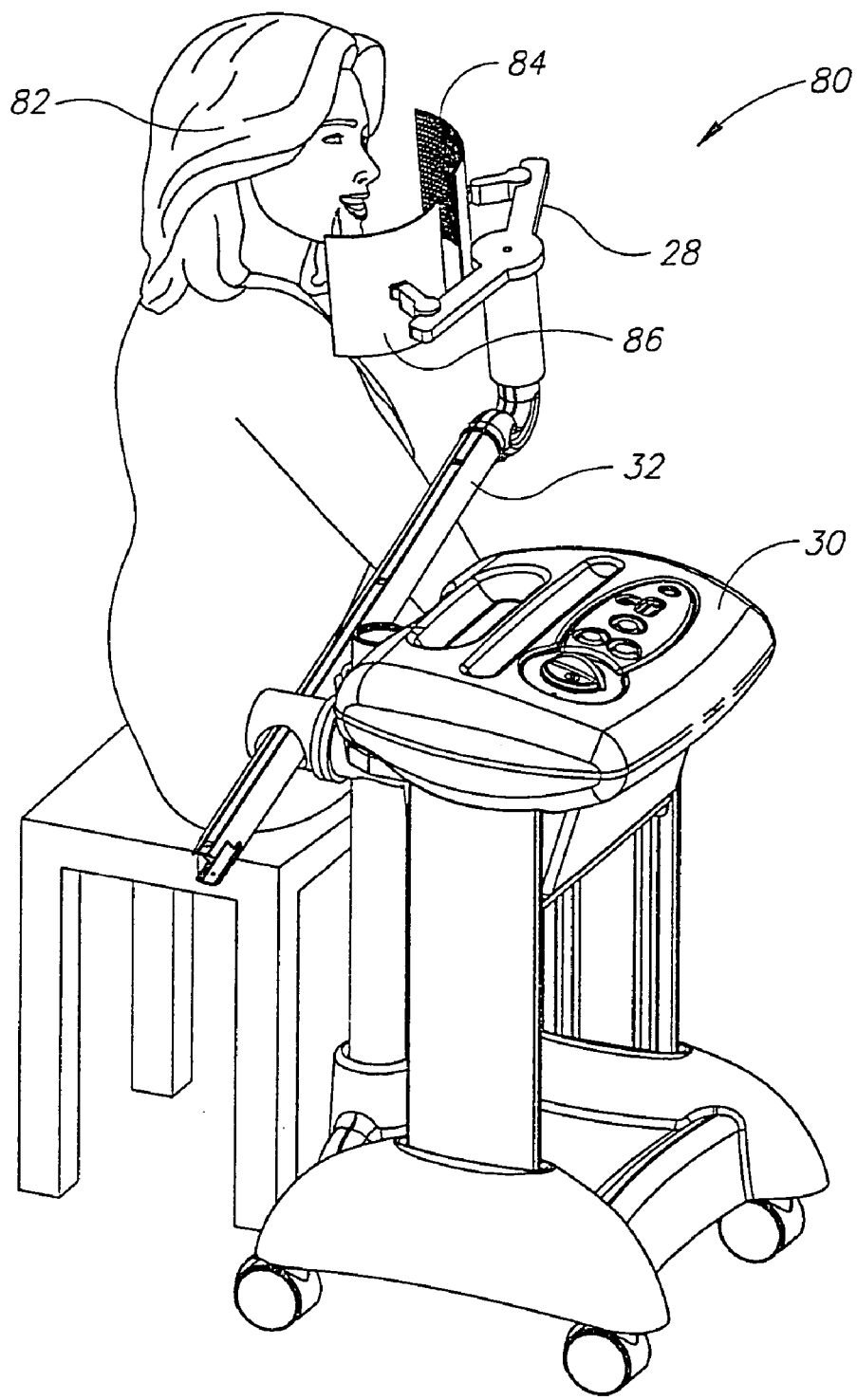
FIG. 5 is a schematic, pictorial illustration of a system for phototherapy, in accordance with an alternative embodiment of the present invention.

FIG. 5 is a schematic, pictorial illustration of a system 80 for phototherapy, in accordance with another embodiment of the present invention. System 80 in this embodiment shown in another treatment application-treating skin inflammation on a face 82 of a patient-but is otherwise functionally similar to system 20. Radiators 84 and 86 in this case comprise panels with multiple miniature solid-state emitters, such as light-emitting diodes (LEDs), mounted on the panels. The emitters may be organized in a single-dimensional or a two-dimensional diode matrix array. As in system 20, both of radiators 84 and 86 typically emit radiation in both the violet/blue and near IR bands. Alternatively, one of the radiators may emit violet/blue radiation, while the other emits IR, either simultaneously or in succession. Greater or smaller numbers of radiators may be used. As a further alternative, one of the radiators may comprise an array of miniature emitters, and the other may comprise a gas discharge lamp, as described above, or a single radiator may comprise both a matrix of miniature emitters and a gas discharge lamp.

Figure 6:
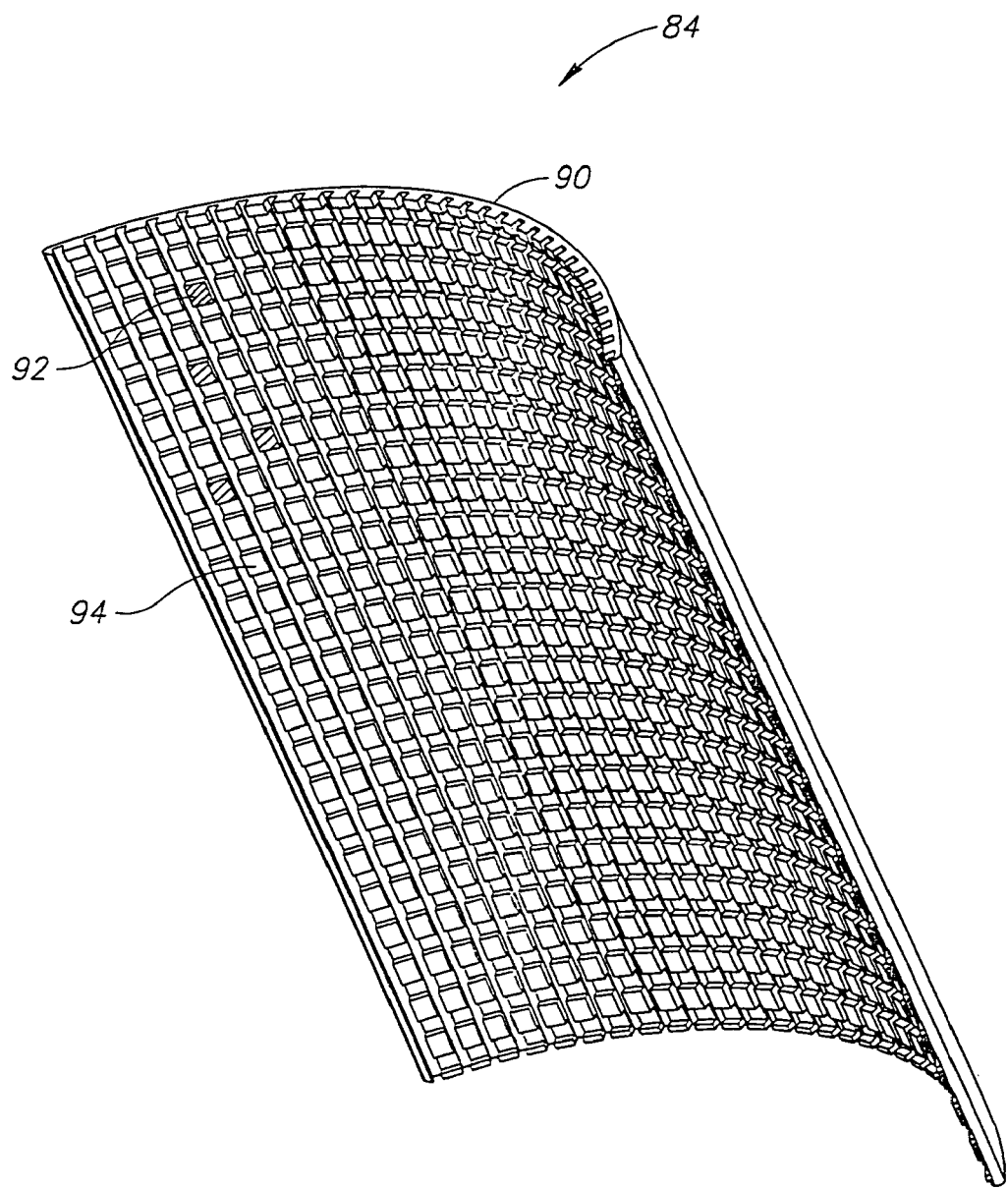
FIG. 6 is a schematic front view of a radiator for use in phototherapy, in accordance with an alternative embodiment of the present invention.

FIG. 6 is a schematic front view of radiator 84, in accordance with an embodiment of the present invention. In this embodiment, the radiator comprises a panel 90, preferably curved, on which a two-dimensional matrix array of high-intensity solid-state radiation sources 92 and 94 are mounted. Typically, sources 92 comprise, GaN, SiN, InSiN or SiC (silicon carbide) based LEDs, or other diode lasers or LEDs of other types that emit violet/blue light. Sources 94 comprise IR-emitting LEDs, such as GaAlAs diodes or GaAs diodes, or laser diodes. The power density requirements of radiator 84 are similar to those of radiator 24, as described above. Suitable violet/blue LEDs are produced, for example, by Nichia Chemical Industries Ltd. (Tokyo, Japan), LumiLED (San Jose, Calif.) and HP/Agilent (PALO ALTO, Calif.). High-intensity IR LEDs are made by many manufacturers, such as LumiLED, Kingbright (Taipei Hesien, Taiwan) and Fairchild Semiconductor (Irvine, Tex.). The LEDs in radiator 84 may be wired and controlled separately or in matrix groups.

Although in the embodiment shown in FIG. 5, radiators 84 and 86 are spaced away from the skin, in other embodiments panel 90 may have the form of a mask, which contacts the skin. The mask might also include thermoelectric cooler elements (TEC) to cool the irradiated skin. The mask may be placed against the skin in combination with a suitable cream or other medication, such as glycolic acid or other antioxidants or peeling creams. Alternatively, the mask may be used without cream or medication. Systems 20 and 80 (and other implementations of the present invention) may be used in treating a wide range of inflammatory skin conditions, including:

Ulcers (as detailed above).

Skin aging, particular in heavy smokers, who tend to have yellowish skin due to reduced blood flow to the skin. These patients' skin suffers from both insufficient capillary supply and chronic subclinical inflammation, both related to the effects of smoking. Chronic exposure to heavily polluted air or excessive sunlight may have similar effects. The skin in these cases may be treated by violet/blue and IR radiation, possibly in combination with fruit acids, such as glycolic acid, and other creams. A course of five to fifteen treatments is expected to visibly improve the skin condition, and can be followed subsequently by periodic maintenance treatments.

Post-surgical edema and redness of the skin. Liposuction, for example, may be followed by marked edema and changes of skin color, which may be relieved by a small number of treatments with violet/blue and IR radiation at high intensity (over 20 mW/cm$^2$ violet/blue and 8 mW/cm$^2$ IR radiation).

Rosacea, grades II and III.

Chronic cutaneous inflammatory conditions, such as atopic dermatitis.

Acne-related inflammations.

Other applications of violet/blue and IR radiation in reducing inflammation will be apparent to those skilled in the art.

Figure 7:
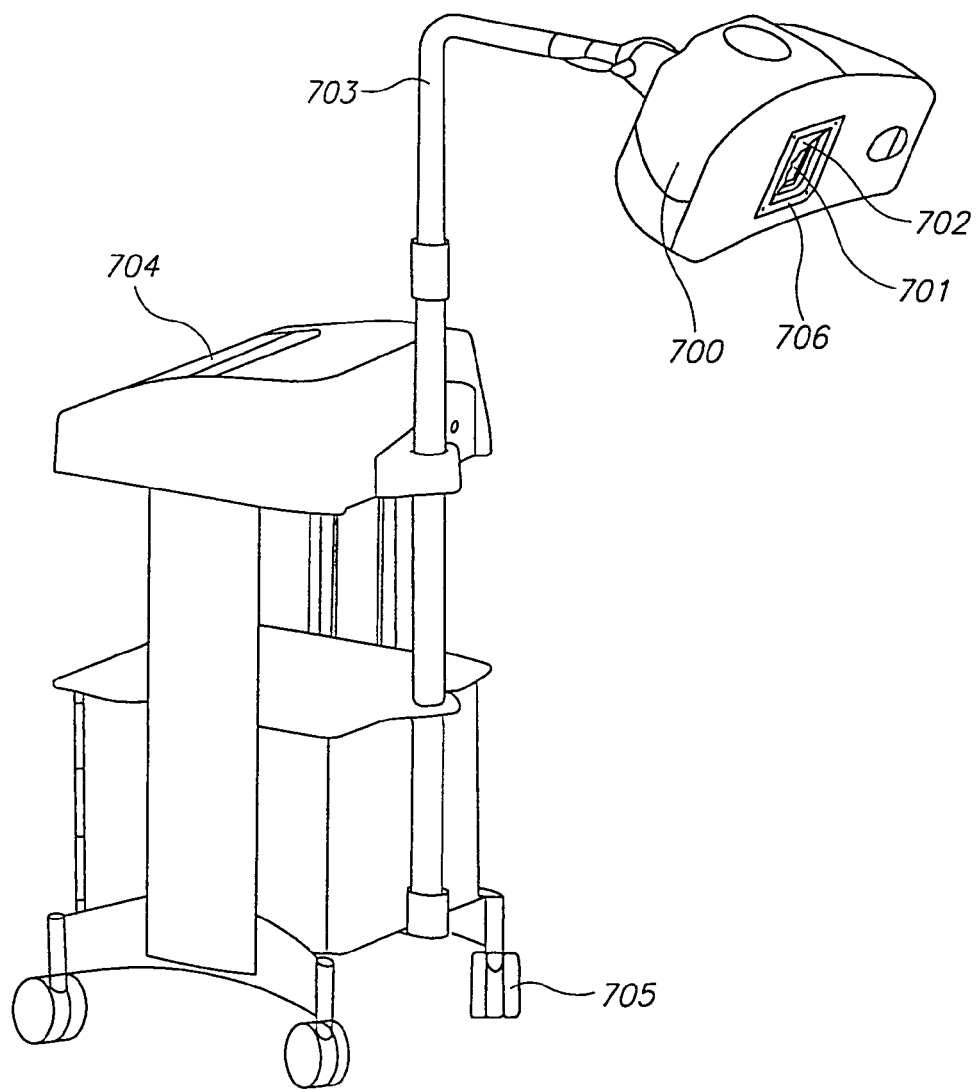
FIG. 7 is a schematic presentation of a commercial unit which utilize the current invention and separately treats each side of the face.

FIG. 7 presents an embodiment of the current invention which has been commercialized and treats each side of the face separately. The treatment head 700 incorporates a light source and a treatment a window 701 which filters UV light and transmits both blue and near infrared light. The treatment head is adjustable and can be aimed at the patient head in sitting or laying position. A removable filter 702 (not drawn) can be added or removed with two screws. The filter transmits blue light and blocks infrared light. The filter is utilized when acne problems are being treated and pure blue light is recommended. The filter is removed when near infrared light and blue light are recommended. The treatment head is attached to a mast 703, the height of which is electrically controlled. An electrical control panel 704 enables the setting of the treatment duration, as well as the turning ON and OFF of an air fan which helps chilling the face.

Figure 8:
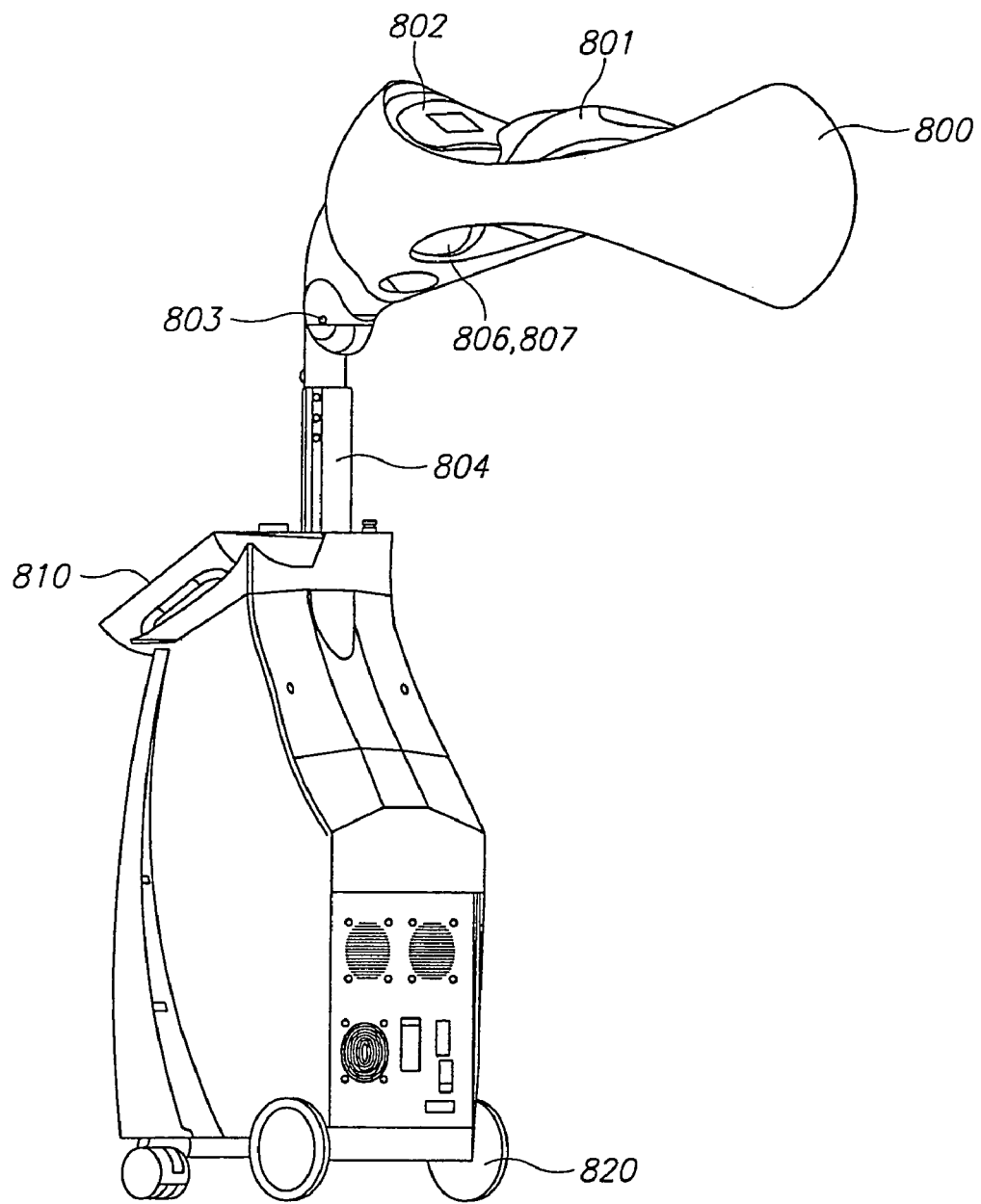
FIG. 8 is a schematic presentation of a commercial unit which utilize the current invention and simultaneously treats both sides of the face.

FIG. 8 presents a system which treats both sides of the face simultaneously. The system incorporates a light head 800 which incorporates two lamps located on both sides of the head. Filters 806 (only one of them is shown in the figure) rejects any UV light and transmits blue and near infrared light. By adding a filter 807 (not shown) which rejects near infrared light to the filter 806, it is possible to provide treatments which require only blue light. The treatment head is attached to a mast 804, the height of which is electrically controlled. A panel 810 enables the control of the treatment duration, the mast height and also serves as a computerized data base which can be fed by patients condition and patient picture. Fans and a camera are located in zone 801. The unit is transportable from room to room and incorporates wheels 820.

EXAMPLE 1

The system has been utilized for the treatment of aging skin in a clinic in Montpelier (France) and a clinic in Tel Aviv (Israel). Over 15 patients have been treated from a distance of 20 cm at a power level of 20 milliwatts/cm$^2$ in both 405–420 nm and 850–890 nm band widths. The number of treatments was 6–8 and combined with Glycolic acid. Results showed clear reduction of pores, pigmentation and improvement of skin color.

EXAMPLE 2

A system was utilized in a clinic for the reduction of the erythema duration after laser skin resurfacing. Normally, post skin resurfacing average erythema duration is 3 weeks. Patients have been treated for 5 days starting one day after skin resurfacing. Erythema faded much faster than without the utilization of the blue/infrared source and lasted only 10 days.

EXAMPLE 3

A system which combines blue and near infrared light was utilized to treat patients immediately after face lifting surgery. A patient was treated with light for 6 days after surgery on one side of the face. The other side was not treated. The treated side doesn't show any redness on the suture line, whereas redness can be seen on the control untreated site. The three examples demonstrate the healing effect of the combination of blue and near infrared light, as utilized by a commercial unit based on the current invention.

Although the embodiments described above are based on certain particular treatment systems and types of radiation sources, the principles of the present invention may similarly be applied in other system configurations and using other suitable radiation sources, as will be apparent to those skilled in the art.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for treating skin conditions with associated inflammation in skin of a patient, comprising irradiating the skin using at least one single radiation source with substantially narrow band infrared (IR) radiation in a first wavelength band and with substantially narrow band violet/blue light in a second wavelength band.

2. The method according to claim 1, wherein the first wavelength band is selected to cause dilation of blood vessels in a vicinity of the inflammation, and wherein irradiating the skin with the violet/blue light comprises applying the violet/blue light to the inflammation while the blood vessels are dilated.

3. The method according to claim 2, wherein irradiating the skin comprises irradiating the skin with the IR radiation and the violet/blue light simultaneously.

4. The method according to claim 2 further comprising sequentially filtering the IR radiation and the violet/blue light with a removable filter so that the skin is treated sequentially with the IR radiation and the violet/blue light.

5. The method according to claim 1, wherein the first wavelength band is in the range 800–980 nm, and the second wavelength band is in the range 405–450 nm.

6. The method according to claim 5, wherein the first wavelength band is in the range 850–900 nm.

7. The method according to claim 1, wherein irradiating the skin comprises irradiating the skin with at least 4 mW/cm$^2$ of the violet/blue light and at least 1 mW/cm$^2$ of the IR radiation.

8. The method according to claim 7, wherein irradiating the skin comprises irradiating the skin with at least 20 mW/cm$^2$ of the violet/blue light and at least 8 mW/cm$^2$ of the IR radiation.

9. The method according to claim 1, wherein irradiating the skin comprises irradiating the skin continuously for at least one minute.

10. The method according to claim 1, wherein irradiating the skin comprises irradiating the skin with pulsed radiation.

11. The method according to claim 1, wherein the at least one single radiation source comprises a discharge lamp containing metal halide materials selected to radiate in the first and second wavelength bands.

12. The method according to claim 1, wherein the skin conditions are selected from the group consisting of skin aging, ulcers, edema, rosacea, chronic cutaneous inflammatory conditions and acne, post surgical healing and reduction of erythema duration in post skin resurfacing.

13. The method according to claim 12, and comprising applying a medicated cream to the skin in conjunction with irradiating the skin.

14. The method according to claim 1, wherein irradiating the skin comprises irradiating the skin using said at least one radiation source that is in contact with the skin.

15. The method according to claim 1 comprising:
(a) positioning in an operative treating position for treating the akin condition and associated inflammation, a self supporting mechanical fixture comprising the at least one single radiation source in a fixed position spaced apart from the skin, said mechanical fixture comprising securing means for operatively securing the at least one single radiation source to the fixture, and adjustment means for adjusting the distance or position of the at least one single radiation source from the skin; and
(b) applying to the skin said substantially narrow band infrared radiation and said substantially narrow band violet/blue light.

16. The method according to claim 1 comprising irradiating the skin with a plurality of single radiation sources.

17. Apparatus for treating skin conditions and associated inflammation in skin of a patient, comprising at least one single radiation source, which is adapted to irradiate the skin with substantially narrow band infrared (IR) radiation in a first wavelength band and with substantially narrow band violet/blue light in a second wavelength band.

18. The apparatus according to claim 17, wherein the at least one single radiation source is adapted to irradiate the skin with the IR radiation and the violet/blue light simultaneously.

19. The apparatus according to claim 17, further comprising removable filter means adapted to sequentially irradiate the skin with the IR radiation and the violet/blue radiation.

20. The apparatus according to claim 17, wherein the first wavelength band is in the range 800–980 nm, and the second wavelength band is in the range 408–460 nm.

21. The apparatus according to claim 20, wherein the first wavelength band is in the range 850–910 nm.

22. The apparatus according to claim 17, wherein the at least one single radiation source is adapted to irradiate the skin with at least 4 mW/cm$^2$ of the violet/blue light and at least 1 mW/cm$^2$ of the IR radiation.

23. The apparatus according to claim 22, wherein the at least one single radiation source is adapted to irradiate the skin with at least 20 mW/cm$^2$ of the violet/blue light and at least 9 mW/cm$^2$ of the IR radiation.

24. The apparatus according to claim 17, wherein the at least one single radiation source is adapted to irradiate the skin continuously for at least one minute.

25. The apparatus according to claim 17, wherein the at least one single radiation source is adapted to irradiate the skin with pulsed radiation.

26. The apparatus according to claim 17, wherein the at least one single radiation source comprises a discharge lamp containing metal halide materials selected to radiate in the first and second wavelength bands.

27. The apparatus according to claim 26, wherein the metal halide materials comprise gallium and cesium halides.

28. The apparatus according to claim 17, wherein the at least one single radiation source comprises a plurality of single radiation sources.

29. The apparatus according to claim 28, further comprising an adjustable bracket, on which the at least one single radiation source is mounted, so as to allow a relative angular orientation of the at least one single radiation source to be adjusted.

30. The apparatus according to claim 17, wherein the at least one single radiation source comprises a spectral filter, for blocking ultraviolet (UV) radiation generated by the at least one single radiation source.

31. The apparatus of claim 30 wherein the spectral filter is contained within the at least one single radiation source.

32. The apparatus of claim 30 wherein the at least one radiation source comprises a window which filters UV light.

33. The apparatus according to claim 17, wherein the at least one single radiation source comprises a forced air cooling device for cooling the skin that is irradiated by the at least one single radiation source.

34. The apparatus according to claim 17, wherein the at least one single radiation source is adapted to be placed in contact with the skin.

35. The apparatus according to claim 17 comprising:
(a) a self supporting mechanical fixture for holding the at least one single radiation source in a fixed position spaced apart from the skin during treatment thereof, said mechanical fixture comprising securing means for operatively securing the at least one single radiation source to the fixture and adjustment means for adjusting the distance or position of the at least one single radiation source from the treatment area, said securing means of the mechanical fixture securing the at least one single radiation source in said fixed position when the at least one radiation source is emitting the radiation and/or light;
(b) an optical system for collecting and shaping the infrared radiation and the violet(blue light in advance of delivering the infrared radiation and the violet/blue light to the skin; and
(c) electronic means for controlling parameters associated with the infrared radiation and the violet/blue light.

36. The apparatus of claim 17 comprising a plurality of single radiation sources.

* * * * *